US011059982B2

(12) United States Patent
Rosset

(10) Patent No.: US 11,059,982 B2
(45) Date of Patent: Jul. 13, 2021

(54) FLUID COMPOSITIONS THAT CAN FORM A COATING HAVING ANTIVIRAL PROPERTIES

(71) Applicant: OBERTHUR FIDUCIAIRE SAS, Paris (FR)

(72) Inventor: Henri Rosset, Le Pin (FR)

(73) Assignee: OBERTHUR FIDUCIAIRE SAS, Paris (FR)

(*) Notice: Subject to any disclaimer, the term of this patent is extended or adjusted under 35 U.S.C. 154(b) by 194 days.

(21) Appl. No.: 13/889,902

(22) Filed: May 8, 2013

(65) Prior Publication Data

US 2014/0155482 A1 Jun. 5, 2014

Related U.S. Application Data

(63) Continuation of application No. PCT/IB2011/054927, filed on Nov. 4, 2011.

(30) Foreign Application Priority Data

Nov. 8, 2010 (FR) ...................................... 1059195

(51) Int. Cl.

*C09D 5/14* (2006.01)
*C09D 11/00* (2014.01)
*A01N 25/04* (2006.01)
*A61L 2/18* (2006.01)
*A61L 2/232* (2006.01)

(52) U.S. Cl.

CPC .............. *C09D 11/00* (2013.01); *A01N 25/04* (2013.01); *A61L 2/18* (2013.01); *C09D 5/14* (2013.01); *A61L 2/232* (2013.01)

(58) Field of Classification Search

CPC A01N 25/04; A61L 2/18; A61L 2/232; C09D 11/00; C09D 5/14

See application file for complete search history.

(56) References Cited

U.S. PATENT DOCUMENTS

| | | | | |
|---|---|---|---|---|
| 1,996,707 | A | 4/1935 | Nathansohn et al. | |
| 3,738,995 | A | 6/1973 | Adams et al. | |
| 4,570,629 | A | 2/1986 | Widra | |
| 4,662,403 | A | 5/1987 | Hammer et al. | |
| 4,764,418 | A | 8/1988 | Kuenn et al. | |
| 4,908,209 | A | 3/1990 | McIntosh, Jr. et al. | |
| 4,929,498 | A | 5/1990 | Suskind et al. | |
| 4,950,685 | A | 8/1990 | Ward | |
| 5,039,339 | A | 8/1991 | Phan et al. | |
| 5,177,128 | A | 1/1993 | Lindemann et al. | |
| 5,217,576 | A | 6/1993 | Van Phan | |
| 5,709,870 | A | 1/1998 | Yoshimura et al. | |
| 5,709,976 | A | 1/1998 | Malhotra | |
| 5,786,282 | A | 7/1998 | Carter et al. | |
| 5,968,538 | A | 10/1999 | Snyder, Jr. | |
| 6,197,805 | B1 | 3/2001 | Smith | |
| 6,262,097 | B1 | 7/2001 | Kovacevic | |
| 6,524,508 | B1 | 2/2003 | Ohnishi et al. | |
| 8,193,244 | B1 | 6/2012 | Stockel et al. | |
| 2002/0068013 | A1 | 6/2002 | Wilcox et al. | |
| 2004/0023008 | A1 | 2/2004 | Rosset | |
| 2004/0109853 | A1* | 6/2004 | McDaniel | 424/94.6 |
| 2005/0043402 | A1* | 2/2005 | Thormar et al. | 514/547 |
| 2005/0175712 | A1 | 8/2005 | Jayet-Laraffe et al. | |
| 2006/0030512 | A1* | 2/2006 | Hart | C11D 1/835 510/481 |
| 2008/0171804 | A1 | 7/2008 | Krishnan | |
| 2008/0279959 | A1 | 11/2008 | Holmes | |
| 2009/0105195 | A1* | 4/2009 | O'Brien | A01N 25/04 514/56 |
| 2010/0056628 | A1* | 3/2010 | Stockel | A01N 25/30 514/551 |
| 2012/0114725 | A1 | 5/2012 | Rosset | |

FOREIGN PATENT DOCUMENTS

| | | | |
|---|---|---|---|
| CN | 101698769 | A | 4/2010 |
| EP | 0059056 | A1 | 9/1982 |
| EP | 0251132 | A1 | 1/1988 |
| EP | 0191217 | B1 | 3/1988 |
| EP | 0749848 | A1 | 12/1996 |
| EP | 1138314 | A2 | 10/2001 |
| EP | 0866103 | B1 | 2/2003 |
| EP | 2160946 | A1 | 10/2010 |
| JP | 51101124 | A | 9/1976 |
| JP | 54041326 | A | 4/1979 |
| JP | 61181390 | A | 8/1986 |

(Continued)

OTHER PUBLICATIONS

Ozcan, Antimicrobial activity of the essential oils of Turkish plant spices, Eur. Food Res. Technol., 2001,212, pp. 658-660.*

A review of Monolaurin and lauric acid, Alternative & complementary therapies—Dec. 2006, vol. 12, pp. 310-315.

Effects of Essential Oils and Monolaurin on *Staphylococcus aures*: In vitro and in Vivo Studies, Toxicology mechanisms and methods, vol. 15, pp. 279-285.

(English Abstract of) "Enzymatic synthesis of decanoic acid monoglycerides", Chinese Journal of Process Engineering, vol. 4, No. 1, Feb. 2004.

(English Translation of) Office Action issued in the correspondencing Chinese proceeding dated Jan. 7, 2015.

(Continued)

*Primary Examiner* — Savitha M Rao
*Assistant Examiner* — Andrew P Lee
(74) *Attorney, Agent, or Firm* — Jones Robb, P.L.L.C.

(57) ABSTRACT

The aim of the present invention is to provide a fluid composition that can form a coating, said composition being characterized in that it contains, at least in a solvent medium, an effective amount of at least one natural virucide selected from among lauric acid, monolaurin, lactoferrin and essential oils having antiviral activity and/or one of the precursors thereof, said composition having a viscosity of 30 mPa·s to 40 Pa·s at room temperature and pressure.

21 Claims, No Drawings

(56) References Cited

FOREIGN PATENT DOCUMENTS

| | | | |
|---|---|---|---|
| JP | 04356404 | A | 12/1992 |
| JP | 05139918 | A | 6/1993 |
| JP | 07292742 | | 11/1995 |
| JP | 0967797 | A | 3/1997 |
| JP | 09119096 | A | 5/1997 |
| JP | 9188892 | A | 7/1997 |
| JP | 10259326 | | 9/1998 |
| JP | 11071211 | A | 3/1999 |
| JP | 2009527357 | A | 7/2009 |
| RU | 92012302 | A | 12/1992 |
| RU | 2181583 | C1 | 4/2002 |
| RU | 2195473 | C1 | 12/2002 |
| RU | 2303615 | C2 | 7/2007 |
| RU | 2338765 | C1 | 11/2008 |
| WO | 1999042658 | A1 | 8/1999 |
| WO | 2000018577 | A1 | 4/2000 |
| WO | 2000049219 | A1 | 8/2000 |
| WO | 2000071183 | A1 | 11/2000 |
| WO | 03/084326 | A2 | 10/2003 |
| WO | 2005022998 | A2 | 3/2005 |
| WO | 2005056449 | A1 | 6/2005 |
| WO | 2006/008566 | A1 | 1/2006 |
| WO | 2007044398 | A2 | 4/2007 |
| WO | 2007100654 | A2 | 7/2007 |
| WO | 2007100654 | A2 | 9/2007 |
| WO | 2008127416 | A2 | 10/2008 |
| WO | 2010/128487 | A2 | 11/2010 |

OTHER PUBLICATIONS

Republic of Kazakhstan office action for Application No. 2013/1552.1 filed on Apr. 11, 2011.

Thormar, Halldor et al., Inactivation of Enveloped Viruses and Killing of Cells by Fatty Acids and Monoglycerides. Antimicrobial Agents and Chemotherapy, Jan. 1987, vol. 31, No. 1, p. 27-31.

International Search Report for PCT/IB2011/054927 dated Mar. 20, 2012.

N. M. Clarke, Effect of antimicrobial factors in human milk on rhinoviruses and milk-borne cytomegalovirus in vitro. J. Med Microbiol. vol. 49 (2000) p. 719-723.

Loizzo, Monica R., Phytochemical Analysis and in vitro Antiviral Activities of the Essential Oils of Seven Lebanon Species. Chemistry & Biodiversity, vol. 5 (2008), p. 461-470.

Seganti, Lucilla et al., Antiviral Activity of Lactoferrin Towards Naked Viruses. BioMetals, vol. 17, (2004) p. 295-299.

Preliminary Search Report for Application No. FA 744247 and FR 10591295 with a filing date of Aug. 11, 2010.

Written Opinion of the International Searching Authority for International Application No. PCT/IB2011/054927 with an International filing date of Apr. 11, 2011.

Mosselman Chemical Data sheet for Glyceryl Monolaurate > 90%. Belgium. Date Accessed Sep. 27, 2016. www.mosselman.be.

Machine Translation of JP 9188892, with a publication date of Jul. 22, 1997.

European Office Action for corresponding Application No. 11 797 364.4 dated Oct. 31, 2016.

Tipvarakarnkoon et al., Rheological properties and phase change behaviors of coconut fats and oils, Annual Transactions of the Nordic Rheology Society, vol. 16, 7 pages, 2008.

Pereira, et al. "Enzymatic Synthesis of Monolaurin", Applied Biochemistry and Biotechnology, 2004, vol. 113-116, pp. 433-445.

Environmental impact of euro banknotes' from the European Central Bank, Dec. 20, 2007.

American Society for Testing and Materials, "Test method for determining the antimicrobial activity of immobilized antimicrobial agents under dynamic contact conditions," ASTM Method E 2149-01, vol. 11.05, Oct. 2001.

Argy, et al. "Study of prophylaxis by didecyl dimethyl ammonium chloride against herpes simplex virus infection in nude mice", C R Acad Sci III., Oct. 1999; 322 (10): 863-70. (Abstract Only).

Association Francaise de Normalisation, "Characterization and measurement of the bacteriostatic activity of fabrics and polymer surfaces with antibacterial properties," AFNOR Method XP G39-010, May 2000.

Dreikorn, "Agricultural Fungicides," (1994) and McEntee, "Industrial Antimicrobial Agents," (1995) in Kirk-Othmer Encyclopedia of Chemical Technology, Wiley, 2000 Online Edition.

International Search Report and Written Opinion for International Application No. PCT/IB2010/052028 dated May 4, 2011.

Kumar "A review of chitin and chitosan applications", Reactive and Functional Polymers, 2000, vol. 46, pp. 1-27.

Marquez-Alvarez, et al. "Solid catalysts for the synthesis of fatty esters of glycerol, polyglycerols and sorbitol from renewable resources", Topics in Catalysis, 2004, vol. 27 (1-4), pp. 105-117.

Periera, et al. "Enzymatic Synthesis of Monolaurin" Proceedings of the Twenty-Fifth Symposium on Biotechnology for Fuels and Chemicals Held May 4-7, 2003, in Breckenridge, CO. 2004. (Abstract Only).

Preliminary Search Report for French Priority Application No. 09 53053 (FR Appin No. 722018) dated Nov. 30, 2009.

Hierholzer et al., In vitro effects of monolaurin compounds on enveloped RNA and DNA viruses, Journal of Food Safety, 4, pp. 1-12, Year: 1982.

Dawson et al., Effect of lauric acid and nisin-impregnated soy-based films in the growth of Listeria monocytogeners on turkey bologna, Poultry Science, vol. 81:5 (721-726), Year: 2002.

* cited by examiner

FLUID COMPOSITIONS THAT CAN FORM A COATING HAVING ANTIVIRAL PROPERTIES

CROSS REFERENCE TO RELATED APPLICATIONS

This application is a continuation of and claims priority to prior filed International Application, Serial No. PCT/IB2011/054927, entitled "Fluid Compositions That Can Form a Coating Having Antiviral Properties", filed Nov. 4, 2011, which claims priority to French Provisional Patent Application No. 10 59195, entitled "Fluid Compositions That Can Form a Coating Having Antiviral Properties", filed on Nov. 8, 2010, the contents of each of which are herein incorporated by reference.

FIELD OF THE INVENTION

The invention relates to fluid compositions capable of forming, on the surface of a support, a coating, in particular a varnish, an ink, a lacquer or a paint, advantageously endowed with antiviral properties.

The field of the invention is more particularly that of compositions intended to be applied on the surface of a flexible or solid support with a view to making a protective layer and/or figurative layer and/or esthetic layer and/or a pattern appear thereon.

BACKGROUND OF THE INVENTION

In modern societies, an increasingly large amount of materials or articles that come under the field of application of the invention is dedicated to being handled daily and frequently by a large number of people.

By way of nonlimiting illustration of these articles, mention may especially be made of substrates, in particular banknotes or cards such as smart cards, or plastic articles such as, for example, toys, computer keyboards and mice, touch screens and telephone keypads, screens and handsets, care, medical or health instruments, fingernails, musical instruments, uniforms, tools, upholstery fabrics.

For obvious reasons, the users of these articles may be carrying viruses, liable to generate more or less serious epidemic and pandemic diseases and, in this way, may be liable to contaminate any article they come into contact with. However, when this article is dedicated to being consecutively handled by one or more other users, it in turn becomes an important vehicle for disseminating, with regard to other people, the virus carried by the first user.

Consequently, it would be advantageous to be able to neutralize, within a short time, any virus in contact with an article or substrate dedicated to multiple use.

For obvious reasons, this neutralization method must, on the one hand, be effective and, on the other hand, have a prolonged duration over time. Moreover, it must be easy to implement and as far as possible not adversely affect the use of the article in question.

SUMMARY OF THE INVENTION

Against all expectations, the inventors have observed that the aforementioned objectives are satisfied via the use of an antiviral fluid composition capable of forming a coating.

Thus, the invention relates, according to one of its aspects, to a fluid composition capable of forming a coating, characterized in that it contains an effective amount of at least one virucide and/or a precursor thereof, said composition having a viscosity between 30 mPa·s and 40 Pa·s, at room temperature and ambient pressure.

The invention relates, according to another of its aspects, to a fluid composition capable of forming a coating, characterized in that it contains an effective amount of at least one virucide of natural origin chosen from monolaurin, lauric acid, lactoferrin and essential oils having an antiviral activity and/or a precursor thereof, said composition having a viscosity between 30 mPa·s and 40 Pa·s, at room temperature and ambient pressure.

Within the meaning of the invention, room temperature is understood to be a temperature varying from 18 to 25° C.

The invention relates in particular to a fluid composition capable of forming a coating on the surface of materials or a substrate, and more particularly intended to cover the articles liable to carry viruses, especially children's toys, fingernails (antiviral nail varnish) or else care, medical or health instruments, banknotes or cards such as smart cards.

Thus, according to another of its aspects, the invention relates to articles, in particular as described above, characterized in that they are capable of being obtained by a process comprising at least one step of surface coating using a fluid composition containing an effective amount of at least one virucide of natural origin chosen from monolaurin, lauric acid, lactoferrin and essential oils having an antiviral activity and/or a precursor thereof, said composition having a viscosity between 30 mPa·s and 40 Pa·s at room temperature and ambient pressure.

According to one of its aspects, the coating step described above is carried out be spraying, printing, overprinting, surface application, coating or deposition of the composition according to the invention on the surface.

Generally, the virucide required according to the invention is formulated in a solvent medium, especially as defined below.

As emerges from the examples below, the virucides considered according to the invention prove advantageous beyond their biological activity.

Firstly, they lend themselves to solubilization in solvent media conventionally considered for the surface treatment of supports, and which are very often aqueous solvents or UV crosslinking resins.

Furthermore, the corresponding solutions and in particular the aqueous or UV crosslinking solutions retain their original color appearance. In other words, if the solvent medium is innately colorless, this same medium formulated with the virucide retains this transparency.

Therefore, in the case of a varnish, the coating that it forms on the surface of a support is both effective and may be completely transparent, subject to the nature of the solvent medium used.

This pseudo-invisibility of the coating is, for obvious reasons, particularly advantageous. In particular, the varnish according to the invention proves particularly advantageous for forming overprint varnishes for information carriers such as banknotes. They do not block the visibility of the security elements integrated into these banknotes.

Similarly, in the case of an ink, paint or lacquer, the presence of a virucide according to the invention does not prove prejudicial to the color effect sought at the same time by way of the associated pigment(s).

Furthermore, the inventors have observed that the virucidal activity of the coatings formed according to the invention on the surface of a support does not turn out to be impaired by prolonged exposure to light or to UV light.

Finally, as explained in detail below, the virucidal efficacy is obtained with reduced concentrations of virucide(s). Surprisingly, an amount of less than 3% or even 2% by weight of virucides expressed by dry weight of the coating containing it, in particular a varnish, proves particularly effective.

According to one particular variant, the compositions according to the invention also contain, in addition, at least one humectant.

The compositions considered according to the invention are more particularly varnishes, inks, lacquers or paints.

According to one embodiment, the compositions considered according to the invention are varnishes, and more particularly overprint varnishes.

Consequently, the compositions according to the invention may contain, besides the virucide or a precursor thereof, at least one of the components conventionally considered in formulations of this type.

Thus, the binders are compounds conventionally used in compositions of varnish and/or ink type. They generally have the role of dispersing particles such as the pigments, if present, within the composition and of contributing, after drying and/or crosslinking of the composition applied to the surface of a support, to the formation of a film of sufficient hardness to give the latter durability.

Against all expectations, the inventors have in fact observed that it is possible to reconcile the presence, within one and the same composition, of two types of compounds as different as a binder and a virucide without being detrimental to their respective efficacies.

The compositions according to the invention may therefore advantageously contain, in addition, at least one binder and, where appropriate, at least one pigment.

The invention also relates, according to another of its aspects, to a process useful for imparting virucidal properties to all or part of the surface of a flexible or solid support comprising at least the step that consists in applying to said surface a composition as defined above.

Generally, the expected coating is obtained at the end of the drying operation of the composition applied. According to one embodiment variant, the drying operation of the composition applied is a UV drying operation. According to this embodiment, the inks or the varnishes obtained will be described as "UV" varnish or "UV" ink.

According to one preferred embodiment variant, the virucide is a virucide of natural origin, especially as defined below.

According to one embodiment variant, the virucide may be generated in situ from a composition according to the invention containing, as active agent, a precursor form of this virucide.

Thus, the invention also relates to a process characterized in that it comprises the application of a composition containing at least one precursor of a virucide, in particular of natural origin, as defined above and the generation of said virucide in situ on the surface of the flexible or solid support.

The invention also relates to a process as defined above, characterized in that said virucide is the monolaurin synthesized in situ by reaction of lauric acid and glycerol in the presence of a catalyst.

DETAILED DESCRIPTION OF THE PREFERRED EMBODIMENT

Fluid Composition

As emerges from the aforegoing, a fluid composition according to the invention has a viscosity between 30 mPa·s and 40 Pa·s, in particular between 50 mPa·s and 25 Pa·s, measured at room temperature and ambient pressure.

The viscosities of the compositions may be measured by conventional methods. The selection of the suitable measurement method and also the suitable measurement apparatus, especially with regard to the viscosity scale of the composition in question, clearly comes under the competences of those skilled in the art. For example, for a composition having a viscosity manifestly of less than 2 Pa·s, the favored measurement apparatus is a Brookfield viscometer with spindle no. 2 at 100 rpm (ISO 2555).

This viscosity may be adjusted with respect to the particular function attached to the composition to namely be formed, for example a varnish, an ink, a lacquer or a paint, but also with respect to the application method considered for treating the surface of a support with said composition. For example, a fluid composition according to the invention may be deposited on the surface of a support by offset printing, gravure printing, by flexography, by flexographic overprinting, by intaglio printing, by typography or by lithography.

Thus, at room temperature and ambient pressure, a fluid composition according to the invention used: in gravure printing may advantageously have a viscosity between 30 and 50 mPa·s; in flexography may advantageously have a viscosity between 30 and 90 mPa·s; in flexographic overprinting may advantageously have a viscosity between 30 and 50 mPa·s; in intaglio printing may advantageously have a viscosity between 9 and 25 Pa·s; in offset printing may advantageously have a viscosity between 2 and 40 Pa·s; and in lithography may advantageously have a viscosity between 10 and 20 Pa·s.

The viscosity of the fluid composition according to the invention may be adjusted via the nature and/or amount of solvent medium associated with the virucide required according to the invention, or else via the addition and the adjustment of the amount of binder(s), if present, according to the invention and in which the virucide or virucide precursor required according to the invention is formulated.

Virucide

The fluid composition capable of forming a coating in accordance with the invention contains at least one virucide and/or precursors thereof. Within the meaning of the present invention, the term "virucide" denotes any compound having the ability to kill or inhibit viruses.

The virucide according to the present invention is more particularly dedicated to killing and/or inhibiting a virus that is pathogenic with regard to mammals and more particularly man. Such viruses may be naked viruses or enveloped viruses.

By way of representation of viruses that are pathogenic for man which are likely to be considered according to the invention, mention may more particularly be made of retroviruses, cytomegaloviruses, rotaviruses, paramyxoviruses, polioviruses, hantaviruses, coxsackieviruses, the encephalomyocarditis virus, picornaviruses including rhinoviruses, DNA or RNA viruses especially flaviviridae, the AIDS virus, influenza viruses, the smallpox virus, the yellow fever virus, the hepatitis C virus, the herpes viruses, the Epstein-Barr virus, the varicella-zoster virus, the rubella virus, or else simian virus 40 or SV40.

The virucides suitable for the invention may be synthetic or of natural origin. By way of illustration of synthetic virucides, mention may especially be made of chlorinated derivatives and aldehydes. They may more particularly be glutaraldehyde, potassium peroxomonosulfate, sodium perborate, potassium peroxodisulfate and sodium percarbonate.

Preferably, the virucide is of natural origin. The expression "virucide of natural origin" is understood to mean any virucide pre-existing in nature or which can be synthesized from natural compounds that exist in nature. The virucides of natural origin that can be used within the context of the present invention may thus be obtained either by extraction and purification starting from a natural medium containing them, or by synthesis from natural compounds. By way of example of such virucides, mention may especially be made of lauric acid, or monolaurin which may be obtained by synthesis from glycerol and lauric acid. In the case of this second alternative, the glycerol and lauric acid constitute, within the meaning of the invention, a virucide precursor in so far as they make it possible, at the end of the process according to the invention, to generate a flexible or solid support with antiviral properties.

More specifically, the term "precursor" denotes, according to the invention, a compound which is able, during the steps of the application process according to the invention, either by conversion or by reaction with another compound which is associated with it, and therefore also described as a precursor, to generate the expected virucide.

According to one embodiment, the virucide may especially be chosen from lauric acid, monolaurin, lactoferrin and essential oils having an antiviral activity, such as, for example, laurel essential oil.

Within the meaning of the invention, the term "monolaurin" is understood to denote both naturally pre-existing monolaurin and that obtained by synthesis from glycerol and lauric acid.

These three types of virucide of natural origin have in fact been identified as exhibiting particularly advantageous properties for the preparation of fluid compositions capable of forming a coating such as are considered within the context of the present invention.

Within the context of the present invention, preferably, the synthesis of monolaurin from lauric acid is carried out at a temperature of around 100° C., preferably greater than or equal to 100° C., so that it may especially be produced during the preparation of varnish in the ovens or else during the crosslinking or drying of inks.

The fluid composition capable of forming a coating in accordance with the invention contains an effective amount of at least one virucide and/or at least one precursor thereof, i.e. a sufficient amount of the latter to endow the composition incorporating it with antiviral properties.

According to one embodiment, it may especially be a sufficient amount of virucide to give said composition incorporating it an antiviral activity of greater than 1 log, according to the measurement protocol described in the examples.

For obvious reasons, the amount of virucide to be used according to the invention depends especially on the nature of said virucide and/or on the nature of said composition and may therefore vary to a large extent.

Those skilled in the art may easily, on the basis of their general knowledge, determine the appropriate amounts. The adjustment of the amount of virucide falls under the competences of those skilled in the art.

The inventors have especially determined that an amount of virucide of less than 2% by weight makes it possible to obtain a satisfactory antiviral activity.

By way of illustration, the fluid composition in accordance with the invention may contain from 0.1% to 3% by dry weight, for example from 0.1% to 2% by dry weight, for example from 0.5% to 1.5% by dry weight, of virucide relative to its total weight.

According to one embodiment, the fluid composition in accordance with the invention may also contain other additional active compounds, which may or may not have an antiviral activity.

It may especially also contain biocides, and for examples biocides of bacteriostatic and/or bactericidal and/or fungistatic and/or fungicidal type. Thus, according to one embodiment, the composition according to the invention contains, besides the required virucide, at least one bactericide and/or one fungicide.

By way of illustration of bactericides, mention may especially be made of refractory silver salts, quaternary ammonium salts such as myristyldimethyhbenzyl-ammonium chloride or alkyldimethylbenzylammonium saccharinate, pyrithiones and derivatives thereof. Preferably, the composition does not comprise a toxic bactericide. In particular, it is free of pyrithiones and derivatives thereof.

By way of illustration of fungicides, mention may especially be made of diiodomethyl-p-tolylsulfone or 3-iodopropargyl-N-butylcarbamate. Preferably, the composition does not comprise a toxic fungicide. In particular, it is free of diiodomethyl-p-tolylsulfone.

According to another embodiment, the virucide required according to the invention may itself exhibit, besides its antiviral activity, at least one other biological activity. Thus, the virucide required according to the invention may for example also exhibit a bacteriostatic, bactericidal, fungistatic or fungicidal activity, and more particularly a bacteriostatic or bactericidal activity.

As specified above, the virucide may be used in a form combined with a humectant.

Humectant

Within the meaning of the invention, a humectant is a compound capable of providing a hydrating or else hygroscopic effect.

Against all expectations, the inventors have observed that the presence of such a compound may make it possible to stimulate the antiviral activity of the virucide, in particular of an associated virucide of natural origin, and therefore to increase the antiviral activity displayed by a fluid composition in accordance with the invention incorporating these two compounds.

By way of representation of these humectants, compounds of polyol type, such as, for example, glycerin, also known as glycerol, propylene glycol, polyethylene glycol, butylene glycol, glyceryl triacetate, or else sorbitol may very particularly be considered, within the context of the present invention.

According to one preferred embodiment variant, the humectant considered is glycerol.

According to another embodiment variant, the humectant considered is chosen from the following compounds: pidolic acid (PCA) and derivatives thereof (arginine PCA, copper PCA, ethylhexyl PCA, lauryl PCA, magnesium PCA, sodium PCA, zinc PCA, etc.); calcium gluconate; fructose, glucose, isomalt, lactose, maltitol, mannitol, polydextrose, sorbitol, saccharose or xylitol; glycyrrhizic acid and derivatives thereof; histidine; hyaluronic acid and salts thereof such as sodium hyaluronate; silk, keratin or soybean hydrolysates; phytantriol; silk; or urea.

The fluid composition in accordance with the invention may contain from 0.5% to 4% by dry weight, for example from 1% to 3% by dry weight of humectant(s), and especially of glycerol, relative to its total weight.

According to one preferred embodiment, the humectant is present in the fluid composition capable of forming a coating in accordance with the invention in a weight ratio of the mass of humectants(s) to the mass of virucide(s) at least equal to 1.

According to one particular embodiment, the fluid composition in accordance with the invention may contain at least one virucide according to the present invention, at least one humectant, especially glycerol, and also at least one bacteriostatic and/or bactericidal biocide or one fungistatic and/or fungicidal biocide.

According to another particular embodiment, the fluid composition in accordance with the invention may contain at least one precursor of the virucide according to the present invention, at least one humectant, especially glycerol, and also at least one bacteriostatic and/or bactericidal biocide and at least one fungistatic and/or fungicidal biocide.

The virucide and/or a precursor thereof and the humectant, if present, are advantageously formulated in a solvent medium.

Solvent Medium

The nature of this solvent medium is directly linked to the type de composition targeted. The solvent medium may be a single-phase or two-phase medium. For example, a solvent medium according to the invention may be in the form of an oil-in water or water-in-oil emulsion.

As specified above, the compositions according to the invention are more particularly inks, varnishes, lacquers or paints. More preferably, the compositions according to the invention are inks or varnishes.

Generally, all of these compositions use, as the solvent medium, water, an organic solvent, an oil or a mixture thereof. For example, among the inks, there are aqueous inks, the solvent of which is water, and also "solvent inks", the solvent of which is organic, and fatty inks. The expression "fatty inks" is understood to mean the various inks used for typographic printing, lithographic printing or intaglio printing. Thus, a fluid composition according to the invention may comprise at least one organic solvent medium composed of at least one organic solvent that is volatile at room temperature.

As organic solvent that is volatile or non-volatile at room temperature, mention may be made of: ketones that are liquid at room temperature such as methyl ethyl ketone, methyl isobutyl ketone, diisobutyl ketone, isophorone, cyclohexanone, acetone; alcohols that are liquid at room temperature such as ethanol, isopropanol, butanol, diacetone alcohol, 2-butoxyethanol, cyclohexanol, 2-amino-2-methyl-1-propanol; glycols that are liquid at room temperature such as ethylene glycol, propylene glycol, pentylene glycol, glycerol, 2-amino-2-ethyl-1,3-propanediol; propylene glycol ethers that are liquid at room temperature such as propylene glycol monomethyl ether, propylene glycol monomethyl ether acetate, dipropylene glycol mono-n-butyl ether; short-chain esters (having from 3 to 8 carbon atoms in total) such as ethyl acetate, methyl acetate, propyl acetate, butyl acetate, aryl acetate, isopentyl acetate; alkanes that are liquid at room temperature such as decane, heptane, octane, dodecane, cyclohexane, isododecane; and mixtures thereof.

As regards oils, they may be chosen from: plant oils; purified linseed oil; tung oil, especially for quick-drying inks; soybean oil, especially in the printing field. This oil is valued for the improvement that it provides in pigment wetting; sunflower oil, especially for preparing alkyd resins; rapeseed oil; tall oil; and petroleum distillates.

The compositions according to the invention may also use, as a solvent medium, a UV crosslinkable resin. For example, UV flexographic inks exist that use this type of resin as a solvent medium.

Besides the virucide or virucide precursor, a composition according to the invention contains the components conventionally used in this type of composition. Thus, an ink, a varnish, a lacquer or a paint is generally composed of one or more pigments and a binder.

Binders

As specified above, a fluid composition capable of forming a coating according to the invention generally also contains at least one binder. More particularly, a binder according to the invention is chosen from resins, waxes, and gums.

A resin may especially be chosen from cycloaliphatic epoxy resins, acrylic resins, vinyl resins, ketone resins, polyester resins and aldehyde resins.

A resin may be present in a composition according to the invention in a content between 15% and 60% by weight, preferably between 20% and 40% by weight, relative to the total weight of the composition.

As waxes that can be used according to the invention, mention may be made of: plant waxes such as carnauba wax, candelilla wax, ouricury wax, Japan wax, cocoa butter or cork fiber wax or sugarcane wax; mineral waxes, for example paraffin wax, petrolatum wax, lignite wax or microcrystalline waxes or ozokerites; synthetic waxes including polyolefin waxes especially polyethylene wax, and the waxes obtained by Fischer-Tropsch synthesis; silicone waxes, in particular substituted, linear polysiloxanes; mention may be made, for example, of polyether silicone waxes, alkyl dimethicones or alkoxy dimethicones having from 16 to 45 carbon atoms, alkyl methicones such as the C30-C45 alkyl methicone sold under the trade name "AMS C 30" by DOW CORNING; hydrogenated oils; and/or mixtures thereof.

By way of illustration of waxes suitable for the invention, mention may especially be made of hydrocarbon waxes, such as beeswax, lanolin wax and Chinese insect waxes; rice bran wax, carnauba wax, candelilla wax, ouricury wax, esparto wax, berry wax, shellac wax, Japan wax and sumac wax; montan wax, orange and lemon waxes, microcrystalline waxes, paraffin waxes and ozokerite; polyethylene waxes, the waxes obtained by Fischer-Tropsch synthesis and waxy copolymers, and also esters thereof.

A wax may be present in a composition according to the invention in a content between 0% and 20% by weight, preferably between 0.5% and 15% by weight, relative to the total weight of the composition.

A gum may especially be chosen from gum arabic, gum tragacanth, cassia gum, gamboges gum, shellac, gum sandarac, gum mastic or gum-resin.

The nature of the binder generally conditions the type of varnish, namely cellulose varnishes, polyurethane varnishes, or else acrylic varnishes.

Preferably, a fluid composition according to the invention is an ink and it contains at least one pigment and at least one binder in particular chosen from a polyethylene wax, an acrylic resin and mixtures thereof.

Preferably, a fluid composition according to the invention is a varnish and it contains at least one binder in particular chosen from a polyethylene wax, an acrylic resin and mixtures thereof. Preferably, a fluid composition according to the invention is an overprint varnish and it contains at least one binder in particular chosen from cycloaliphatic epoxy resins.

Pigments

A fluid composition capable of forming a coating according to the invention may advantageously contain one or more pigment(s).

The pigments may be present in a proportion from 0% to 60% by weight, especially from 10% to 50% by weight, and in particular from 15% to 35% by weight, relative to the total weight of the fluid composition capable of forming a coating according to the invention.

Preferably, the fluid composition according to the invention is an ink, and the pigments may be present in a proportion from 0% to 60% by weight, especially from 10% to 50% by weight, and in particular from 15% to 35% by weight, relative to the total weight of the fluid composition capable of forming a coating according to the invention.

The term "pigments" should be understood to mean white or colored, mineral or organic particles, which are insoluble in an aqueous solution and which are intended to color and/or opacify the resulting film.

Mention may be made, as mineral pigments that can be used in the invention, of titanium, zirconium or cerium oxides and also zinc, iron or chromium oxides, ferric blue, manganese violet, ultramarine blue and chromium hydrate.

Mention may be made, as organic pigments that can be used in the invention, of carbon black, D&C type pigments and lakes based on cochineal carmine or on barium, strontium, calcium or aluminum.

According to one embodiment variant, these pigments may also be pearlescent pigments, also known as nacreous pigments, and/or luminescent pigments and in particular fluorescent or phosphorescent pigments.

Mention may be made, as nacreous pigments that can be used in the invention, of titanium-mica coated with an iron oxide, titanium-mica coated with bismuth oxychloride, titanium-mica coated with chromium oxide, titanium-mica coated with an organic dye and also nacreous pigments based on bismuth oxychloride. They may also be mica particles at the surface of which are superposed at least two successive layers of metal oxides and/or of organic dyestuffs. Mention may also be made, as examples of nacreous pigments, of natural mica coated with titanium oxide, with iron oxide, with natural pigment or with bismuth oxychloride.

As inorganic fluorescent substances that can be used in the present invention, mention may for example be made of inorganic fluorescent substances based on zinc oxide, pigments that are fluorescent in daylight, which are generally manufactured from fluorescent dyes that are first dissolved in a support resin in order to obtain a solid solution which is then milled to give a powder of resin particles having fluorescent properties.

The fluorescent pigments suitable for the present invention may be chosen from colored resins of polyamide and/or of formaldehyde/benzoguanamine and/or of melamine/formaldehyde/sulfonamide, from colored aminotriazine/formaldehyde/sulfonamide co-condensates and/or from metalized polyester flakes and/or mixtures thereof. These fluorescent pigments may also be in the form of aqueous dispersions of fluorescent pigments.

When the organic fluorescent substances are white, they are also known as optical brighteners, absorbing essentially in the UVA between 300 and 390 nm and reemitting essentially between 400 and 525 nm.

The compositions may also comprise one or more additives that make it possible to optimize the characteristics of the coating during and after its application. Found among the additives are especially dispersants, antifoaming agents, but also polymers, thickeners and plasticizers.

Application Process

Another subject of the invention relates to a process for applying a fluid composition capable of forming a coating as defined previously.

According to a first embodiment, it may be a process useful for imparting virucidal properties to all or part of the surface of a flexible or solid support comprising at least the step that consists in applying a composition as defined above.

Regarding the incorporation of said virucide, in particular of natural origin, into said composition, it is possible to be led to use particular emulsions or solutions, for example such as ammoniacal solutions or preferably solutions based on 2-amino-2-methyl-1-propanol, which has the advantage of not generating an odorous release.

According to one embodiment variant, the humectant may be present in such an emulsion.

The virucide, in particular of natural origin, may be as defined previously, and may especially be chosen from monolaurin, lactoferrin and an essential oil having an antiviral activity, such as, for example, laurel essential oil.

The humectant may also be as defined previously, and may especially be glycerol.

The application of said composition to the surface of the flexible or solid support to be covered may take place in various ways: by spraying said composition on the surface, by printing said composition on the surface, by overprinting said composition on the at least partially printed surface, by surface application of said composition on the surface, by coating said composition on the surface, and by deposition of said composition on the surface.

The humectant is advantageously present in the fluid composition according to the invention.

In particular, said application of the fluid composition according to the invention may be favored by the use of a monolaurin emulsion.

According to one embodiment variant, the virucide may be generated in situ from a composition according to the invention containing, as active agent, a precursor form of this virucide.

Thus, according to another of its aspects, the invention also relates to a process characterized in that it comprises the application of a composition containing at least one precursor of a virucide, in particular of natural origin, as defined above and the generation of said virucide in situ on the surface of the flexible or solid support, during said application of said composition.

According to one embodiment variant, this process may also comprise the use of a humectant, especially as defined above.

This embodiment variant is particularly suitable when the virucide is of natural origin and when the latter is, for example, easily attainable by synthesis, preferably at costs that are, in addition, advantageous. Thus, it could be, for example, monolaurin synthesized in situ by reaction of lauric acid and glycerol in the presence of a catalyst.

Monolaurin is in fact also available commercially, but at relatively high prices. Its synthesis in situ according to this embodiment variant therefore enables it to be used in a fluid composition of coating type at a reduced cost.

Regarding the incorporation of said virucide into said composition, it may be favored by the use of a solution of lauric acid, especially such as an ammoniacal solution or preferably a solution based on 2-amino-2-methyl-1-propanol, which has the advantage of not generating an odorous release.

According to this second embodiment, the process may comprise at least the steps consisting in:

a) using a flexible or solid support having a surface to be treated that comprises at least one catalyst and/or reactant capable of stimulating the interaction between lauric acid and glycerol;

b) bringing said surface into contact with a fluid composition as defined above containing at least lauric acid and glycerol; and c) subjecting the surface treated in step b) to a heat treatment conducive to the synthesis of monolaurin;

it being possible for said steps b) and c) to be carried out consecutively or simultaneously.

According to another embodiment variant, the catalyst may be present in the fluid composition containing lauric acid and glycerol.

According to one embodiment variant, this process may be carried out in the presence of an antifoaming agent.

More particularly, this is a compound sold under the name Aerotech 3514® (KEMIRA CHIMIE SA) and which is formed from a mixture of mineral oils and nonionic surfactants. Such a compound may be introduced at a concentration between 0.01% and 0.30%, preferably between 0.04% and 0.20%, and more preferably between 0.04% and 0.12% relative to the total weight of the mixture of lauric acid and glycerol.

As indicated previously, the synthesis of monolaurin from lauric acid and glycerol takes place in the presence of a catalyst. By way of example of a catalyst more particularly suitable for the catalysis of this reaction, mention may especially be made of zeolites, and for example the zeolite A sold by the company FMC Foret, or lipases.

In the case where the catalyst is a lipase, reference may especially be made to the reaction conditions described by Pereira C. C. B., Da Silva M. A. P. and Langone M. A. P. in the publication "*Enzymatic synthesis of monolaurin*" (Applied Biochemistry and Biotechnology, 2004, vol. 113-116, p. 433-445).

By way of a lipase more particularly suitable within the context of the present invention, mention may for example be made of the lipases sold under the references Lipozyme RM IM®, Lipozyme TL IM® and Resinase A2C® by the company NOVOZYMES.

The fluid composition in accordance with the invention may contain from 0.5% to 3% by dry weight, for example from 0.5% to 2% by dry weight, of catalyst relative to its total weight.

The catalyst, for example the zeolite, may be introduced in a proportion of at least 2% by weight, for example at least 5% by weight, relative to the total weight of the mixture of lauric acid and glycerol.

According to a first embodiment variant, the lauric acid and the glycerol may be introduced as an equimolar mixture.

According to a second embodiment variant, the glycerol may be introduced in excess relative to the lauric acid. According to this second variant, residual excess glycerol therefore remains present in the coating at the end of the reaction. As mentioned previously, this residual glycerol may act as humectant and increase the antiviral properties.

The following nonlimiting examples will make it possible to better understand how the invention may be put into practice and the advantages thereof.

Example 1

Preparation of a Monolaurin Emulsion:

50 g of synthetic monolaurin is stirred, using a Rayneri mixer in a water bath at 50° C., until it has melted. 5 g of Disponil TD® 0785 and 7 g of water are added. 4 g of Eumulgin BA® 10, melted at 50° C., are added, then after homogenization, it is left to cool to room temperature with stirring. 6 g of water are added with stirring, then are left stirring for 15 min. 47.5 g of water is slowly introduced with stirring. An emulsion containing 42% monolaurin is obtained.

Flexographic Ink

TABLE I

| | % | % dry |
|---|---|---|
| Slurry Kaolin:Intrafill 60 (dry content 60%) | 33.4 | 20 |
| Joncryl 1674 (dry content 41%) | 56.8 | 23.3 |
| PE Wax Emulsion: Aquacer 2500 (dry content 40%) | 4.8 | 1.9 |
| Antifoam Nopco 8034 | 0.48 | |
| 42% monolaurin emulsion according to example 1 | 4.5 (i.e. 1.9% of monolaurin) | 1.9 |
| Total | 100% | 47.1% |

The preparation is carried out using a Rayneri mixer. The flexographic ink prepared as indicated above is coated onto two faces of a conventional paper support (vellum paper NS 2005 5175). Each face is dried for 3 min at 100° C. The average deposit per face is 14.4 g/$m^2$ wet, i.e. around 6.8 g/$m^2$ dry (0.27 g/$m^2$ of monolaurin).

Overprint Varnish

TABLE II

| | % | % dry |
|---|---|---|
| Joncryl 1674 (dry content 41%) | 62.0 | 26.7 |
| Joncryl 8078 (dry content 32%) | 19.1 | 6.1 |
| PE Wax Emulsion: Aquacer 2500 (dry content 40%) | 6.7 | 2.7 |
| water | 7.6 | |
| 42% monolaurin emulsion | 4.5 (i.e. 1.9% of monolaurin) | 1.9 |
| Total | 100 | 37.4 |

The preparation is carried out using a Rayneri mixer. The overprint varnish prepared as indicated above is coated on two faces of a Polyart® plastic support (uncoated Polyart P3). Each face is dried for 2 min at 90° C. The average deposit per face is 15.8 g/$m^2$ wet, i.e. around 5.8 g/$m^2$ dry (0.30 g/$m^2$ of monolaurin).

Example 2

Antiphage Activity of Support Treated According to the Invention

A test of the antiphage activity is carried out. The test is based on the modified JIS L 1902 standard, or else on the modified ISO 20743 standard, on MS2 phages, which are reputed to be highly resistant, and applied over action times of between 18 and 24 hours.

The principle is the following: MS2 phages are deposited on the conventional paper support (vellum paper NS 2005 5175) considered in the first part of example 1, then the number of active MS2 phages is evaluated a first time at t=0 h, and a second time at t=24 h.

In order to evaluate the number of active MS2 phages on the supports to be tested at a given time, these supports are brought into contact with particular bacteria that have the property of being MS2 phage hosts: the measurement of the number of lysis plaques (or pfp) after culturing then makes it possible to get back to the desired amount of MS2 phages.

It is thus possible to deduce therefrom an antiphage activity (denoted by A), defined as follows:

$A=[\text{av}\log(C_{24})-\text{av}\log(C_0)]-[\text{av}\log(E_{24})-\text{av}\log(E_0)]$, in which formula $E_{24}$ corresponds to the number of lysis plaques at 24 h and $E_0$ corresponds to the number of lysis plaques just after bringing into contact with the support tested.

The experimental conditions are the following:

The diluent used is the peptone/salt (of reference DIFCO, 1897-17) and the bacterial strain used is *Escherichia coli* K12, which is a host strain of MS2 phages. The control support is an untreated 100% cotton textile. 200 μL of a suspension of phages containing $1\times10^5$ pfp/mL are deposited.

The following antiphage activity is deduced therefrom:

$$A_{flexographic\ ink\ according\ to\ example\ 1}=-2.74-(-3.94)=1.20\ \log$$

The results are reported below.

TABLE III

| Sample | specimen | $C_0$ (pfp/sample) | log ($C_0$) | av $C_0$ | log (av $C_0$) | $C_{24}$ (pfp/sample) | log ($C_{24}$) | av $C_{24}$ | log (av $C_{24}$) |
|---|---|---|---|---|---|---|---|---|---|
| | | Incubation time: 0 h | | | | Incubation time: 24 h | | | |
| Control = textile support without ink | 1 | 6 300 000 | 6.80 | 5 580 000 | 6.75 | 4 300 | 3.63 | 10 150 | 4.01 |
| | 2 | 4 860 000 | 6.69 | | | 16 000 | 4.20 | | |

| Sample | specimen | $E_0$ (pfp/sample) | log ($E_0$) | av $E_0$ | log (av $E_0$) | $E_{24}$ (pfp/sample) | log ($E_{24}$) | av $E_{24}$ | log (av $E_{24}$) |
|---|---|---|---|---|---|---|---|---|---|
| | | Incubation time: 0 h | | | | Incubation time: 24 h | | | |
| Support treated with flexographic ink according to example 1 | 1 | 2 900 000 | 6.46 | 4 950 000 | 6.69 | 430 | 2.63 | 560 | 2.75 |
| | 2 | 7 000 000 | 6.85 | | | 690 | 2.84 | | |

Example 3

Antiviral Activity of Support Treated According to the Invention

Two tests of the antiviral activity are carried out, one with respect to Poliovirus Lsc 1 and the other with respect to Influenza A (H1N1).

The support tested is the Polyart® plastic support (uncoated Polyart P3) considered in the second part of example 1.

Poliovirus Lsc 1

The procedure is comparable to the test ASTM E 1053-97 (Standard Test Method for Efficacy of Virucidal Agents Intended for Inanimate Surfaces). The supports are untreated plain papers made of cotton.

The principle is the following:

The treated and untreated papers are cut into 30 $mm^2$ sections. Five of these treated and untreated sections are placed in 250 mm sterile plastic Petri dishes. 100 microliters of a dilution comprising viruses as defined above are applied uniformly to the surface of the square sections. The five dilutions ultimately tested on the support treated according to the invention and the control support are specified in table IV. The Petri dishes are covered and incubated for 24 h at 22° C. They are then withdrawn and each inoculated section is transferred into a sterile conical-bottom centrifuge tube (Fisher Scientific, PA). For each tube, 20 mL of sterile PBS (Phosphate Buffered Saline) and 3% beef extract (Becton Dickinson #263010, MD) are added. The tubes are places on an orbital shaker and shaken at low speed for 15 minutes. After shaking, 5 ml of liquid are withdrawn from each tube, which are each placed in a new sterile conical-bottom centrifuge tube (Fisher Scientific, PA). The suspensions are diluted ten times in PBS. The number of viable polioviruses in each tube is counted. The counting is carried out by aliquot inoculation of the sample dilutions on freshly prepared BGM cell monolayers using an agar coating. The plaques are recorded over a period of 2-4 days of incubation. The cells are incubated at 35° C. in an atmosphere containing 5% $CO_2$. The results are reported below.

TABLE IV

| | Concentration of Poliovirus pfu/ml % | Average percentage reduction in the virus concentration |
|---|---|---|
| Support treated with overprint varnish according to example 1 | 23 | 98.8 |
| Support treated with overprint varnish according to example 1 | 28.5 | |
| Support treated with overprint varnish according to example 1 | 22 | |
| Support treated with overprint varnish according to example 1 | 17 | |
| Support treated with overprint varnish according to example 1 | 10.5 | |
| Control 1 | 170 | 53.9 |
| Control 2 | 650 | |
| Control 3 | 900 | |

TABLE IV-continued

| | Concentration of Poliovirus pfu/ml % | Average percentage reduction in the virus concentration |
|---|---|---|
| Control 4 | 110 | |
| Control 5 | 1100 | |

The initial concentration of infectious viral units per sample is 1700 pfu/ml (pfu=plaque forming units). The results are evaluated after a contact time of 24 h.

Influenza A (H1N1)

Preparation of Virus Cultures:

The Influenza A (H1N1; ATCC VR-1469) virus is propagated and counted as most probable numbers (MPN) using, as hosts, monolayers (ATCC CCL-34) of MDCK (Madin-Darbin Canine Kidney type I) cells. The cells are cultured in 12-well cell culture plates. For the counting, aliquot portions of a sample are inoculated on freshly prepared monolayers of MDCK monolayers. The cells are incubated in a dMEM (MediaTech, USA) medium containing trypsin, at 35° C. and in an atmosphere containing 5% $CO_2$ for 5-7 days. The cells are monitored systematically using a microscope to observe the signs of degeneration. The cells in the wells exhibiting signs of infectiosities (Cytopathic effects; CPE) are recorded as positive (+) and those not exhibiting these signs are recorded as negative (−). The most probable number of infectious viruses in a sample is then calculated using MPNCALC software (version 0.0.0.23).

For the experiments, a frozen viral stock (typically $1\times10^8$ iu/ml) is rapidly defrosted in a water bath at 35° C. the day before the experiments. A 1/10 dilution of the stock in PBS supplemented with 2% BSA (Bovine Serum Albumin) is then carried out. The stock is then used for the following antiviral test. The diluted viral stock is titrated with ten successive dilutions of PBS and inoculated on MDCK cells as described above. The procedure for the antiviral test is the same as that described above. The number of Influenza A viruses in each tube is counted. The counting is carried out according to the MPN procedure described above. The results are reported below.

TABLE V

| | Calculated most probable number (MPN) of Influenza A % | Average percentage reduction in virus concentration |
|---|---|---|
| Support treated with overprint varnish according to example 1 | <0.4 | >99.999 |
| Support treated with overprint varnish according to example 1 | <0.4 | |
| Support treated with overprint varnish according to example 1 | <0.4 | |
| Support treated with overprint varnish according to example 1 | <0.4 | |
| Support treated with overprint varnish according to example 1 | <0.4 | |
| Control 1 | 460 | 98.2 |
| Control 2 | 1100 | |
| Control 3 | 460 | |
| Control 4 | 1100 | |
| Control 5 | 1100 | |

The initial calculated MPN is 460 000 and the number of infectious viral units inoculated per sample is 46 000. The results are evaluated after a contact time of 24 h.

In the preceding specification, all documents, acts, or information disclosed do not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of methods for treatment of stroke, it will be apparent to those skilled in the art that variations and modifications are possible without deviating from the broad spirit and principle of the present invention.

It is also to be understood that the following claims are intended to cover all of the generic and specific features of the invention herein described, and all statements of the scope of the invention which, as a matter of language, might be said to fall there between.

What is claimed is:

1. A fluid composition capable of forming a virucidal coating on a support, the fluid composition comprising:
  - a solvent medium;
  - a biocide, wherein the biocide is monolaurin or lactoferrin, the biocide is the only biocide present in the fluid composition, the biocide is solubilized in the solvent medium, the biocide is present in the fluid composition in an amount from 0.1% w/w to 3% w/w, the biocide is a virucide, and the amount is sufficient to kill or inhibit one or more viruses on the virucidal coating; and
  - a binder selected from the group consisting of one or more resins, one or more waxes, one or more gums, and any combination thereof,
  - wherein the fluid composition has a viscosity from 30 mPa·s to 40 Pa·s, at room temperature and ambient pressure, and the virucidal coating is an ink or a varnish.

2. The fluid composition of claim 1, wherein the biocide kills or inhibits one or more human pathogenic viruses.

3. The fluid composition of claim 1, further comprising a humectant.

4. The fluid composition of claim 3, wherein the humectant is a polyol.

5. The fluid composition of claim 3, wherein weight ratio of mass of the humectant to mass of the virucide is at least equal to 1.

6. The fluid composition of claim 1, wherein the virucidal coating is the ink, the ink comprises a pigment, and the binder is selected from the group consisting of a polyethylene wax, an acrylic resin, and any combination thereof.

7. The fluid composition of claim 6, wherein the ink comprises greater than 0% to 60% w/w of the pigment.

8. The fluid composition of claim 1, wherein the virucidal coating is the varnish, and the binder is selected from the group consisting of a polyethylene wax, an acrylic resin, and any combination thereof.

9. The fluid composition of claim 8, wherein the varnish is an overprint varnish, and the binder is a cycloaliphatic epoxy resin.

10. A method of coating a surface of a support with a virucidal coating, the method comprising:
  - providing a support having a surface to be coated; and
  - applying a fluid composition comprising:
    - a solvent medium,
    - a biocide, wherein the biocide is monolaurin, or lactoferrin, the biocide is the only biocide present in the fluid composition, the biocide is solubilized in the solvent medium, the biocide is present in the fluid composition in an amount from 0.1% w/w to 3% w/w, the biocide is a virucide, and the amount is sufficient to kill or inhibit one or more viruses on the virucidal coating, and virucide a binder selected from the group consisting of one or more resins, one or more waxes, one or more gums, and any combination thereof, wherein the fluid composition has a viscosity from 30 mPa·s to 40 Pa·s, at room temperature and ambient pressure, and the virucidal coating is an ink or a varnish.

11. The method of claim 10, wherein the fluid composition is applied to the surface of the support by a method selected from the group consisting of offset printing, gravure printing, flexography, flexographic overprinting, intaglio printing, typography, lithography, and any combination thereof.

12. A support having a virucidal coating prepared by a process comprising the steps of:

providing the support having at least one surface to be treated; and applying a fluid composition comprising:

a solvent medium, a biocide, wherein the biocide is monolaurin or lactoferrin, the biocide is the only biocide present in the fluid composition, the biocide is solubilized in the solvent medium, the biocide is present in the fluid composition in an amount from 0.1% w/w to 3% w/w, the biocide is a virucide, and the amount is sufficient to kill or inhibit one or more viruses on the virucidal coating, and a binder selected from the group consisting of one or more resins, one or more waxes, one or more gums, and any combination thereof, wherein the fluid composition has a viscosity from 30 mPa·s to 40 Pa·s, at room temperature and ambient pressure, and the virucidal coating is an ink or a varnish.

13. The fluid composition of claim 1, wherein the fluid composition contains from 0.1% to 2% w/w of the virucide.

14. The fluid composition of claim 1, wherein monolaurin is the biocide.

15. The support of claim 12, wherein monolaurin is the biocide.

16. The fluid composition of claim 1, wherein the binder comprises a resin, and the fluid composition contains from 15% to 60% w/w of the resin.

17. The support of claim 12, wherein the binder comprises a resin, and the fluid composition contains from 15% to 60% w/w of the resin.

18. The fluid composition of claim 1, wherein the binder comprises a wax, and the fluid composition contains greater than 0% to 20% w/w of the wax.

19. The support of claim 12, wherein the binder comprises a wax, and the fluid composition contains greater than 0% to 20% w/w of the wax.

20. The fluid composition of claim 1, wherein the biocide kills or inhibits a poliovirus, an influenza virus, or both.

21. The support of claim 12, wherein the biocide kills or inhibits a poliovirus, an influenza virus, or both.

* * * * *